US012758392B2

(12) United States Patent
Rolf et al.

(10) Patent No.: US 12,758,392 B2
(45) Date of Patent: Oct. 13, 2026

(54) EXPANDABLE INTERVERTEBRAL SPINE IMPLANT AND METHODS OF USING THE SAME

(71) Applicant: Diagon Medical Inc., Long Beach, CA (US)

(72) Inventors: Joseph Rolf, Long Beach, CA (US); Brion Daffinson, Marietta, GA (US); Austin Howell, Santa Clarita, CA (US); Austin Clemens, Denver, CO (US)

(73) Assignee: Diagon Medical Inc., Long Beach, CA (US)

( * ) Notice: Subject to any disclaimer, the term of this patent is extended or adjusted under 35 U.S.C. 154(b) by 0 days.

(21) Appl. No.: 18/934,238

(22) Filed: Nov. 1, 2024

(65) Prior Publication Data

US 2025/0161064 A1 May 22, 2025

Related U.S. Application Data

(60) Provisional application No. 63/599,809, filed on Nov. 16, 2023.

(51) Int. Cl.
*A61F 2/44* (2006.01)
*A61B 17/80* (2006.01)
*A61F 2/30* (2006.01)

(52) U.S. Cl.
CPC ................ *A61F 2/44* (2013.01); *A61B 17/80* (2013.01); *A61F 2002/30579* (2013.01)

(58) Field of Classification Search
CPC .......... A61F 2/44; A61F 2/4405; A61F 2/442; A61F 2/4455; A61F 2/447; A61F 2002/448; A61F 2/46; A61F 2/4611; A61F 2002/4625; A61F 2002/4629; A61F 2002/30383; A61F 2002/30405; A61F 2002/30411; A61F 2002/30471; A61F 2002/30507; A61F 2002/30538; A61F 2002/4627; A61F 2002/4628; A61F 2002/30556
USPC ..................... 623/17.11–17.16; 606/246–249
See application file for complete search history.

(56) References Cited

U.S. PATENT DOCUMENTS

| | | | | |
|---|---|---|---|---|
| 11,331,197 | B2 | 5/2022 | Shoshtaev | |
| 2016/0256291 | A1 * | 9/2016 | Miller | A61F 2/4611 |
| 2017/0056200 | A1 | 3/2017 | Koch et al. | |
| 2019/0117409 | A1 * | 4/2019 | Shoshtaev | A61F 2/4425 |
| 2019/0358054 | A1 | 11/2019 | Farin | |
| 2021/0137695 | A1 * | 5/2021 | Huang | A61F 2/4455 |
| 2022/0395379 | A1 * | 12/2022 | Ries | A61F 2/44 |

* cited by examiner

*Primary Examiner* — Eduardo C Robert
*Assistant Examiner* — Tara Rose E Carter
(74) *Attorney, Agent, or Firm* — FisherBroyles LLP; Anthony J DoVale

(57) ABSTRACT

An expandable intervertebral spine implants having expandable and angulating side plates controlled by rotating center rod and methods of using the same.

21 Claims, 18 Drawing Sheets

EXPANDABLE INTERVERTEBRAL SPINE IMPLANT AND METHODS OF USING THE SAME

RELATED APPLICATION

This application claims priority to U.S. Provisional Application No. 63/599,809 filed Nov. 16, 2023, hereby incorporated by reference.

TECHNICAL FIELD

The invention generally relates to expandable intervertebral spine implants and methods of using the same.

BACKGROUND

Several publications may be referenced in this application. The cited references describe the state of the art to which this invention pertains and are hereby incorporated by reference, particularly the systems and methods set forth in the detailed description and figures of each reference.

Known methods for handling the pain and discomfort associated with intervertebral spine discs that have become degenerated due to trauma, aging or disease is the use of intervertebral spine fusion implants for fusing one or more adjacent vertebral bodies. Generally, to fuse the adjacent vertebral bodies, the intervertebral disc is first partially or fully removed. An intervertebral fusion implant is then typically inserted between adjacent vertebrae to maintain normal disc spacing and restore spinal stability, thereby facilitating an intervertebral fusion.

The invention relates to improved expandable intervertebral spine implants and methods of using the same.

SUMMARY OF INVENTION

The invention relates generally to devices for fusing adjacent vertebral bodies and methods of using the same.

One aspect of the invention relates to expandable intervertebral spine implants. One embodiment relates to an expandable intervertebral spine implant having an anterior side, a posterior side, a distal end and a proximal end, the implant comprising:

(a) a center rod having a center rod length comprising a proximal threaded portion having a proximal threading direction and a distal threaded portion having a distal threading direction opposite the proximal threading direction;

(b) a proximal sled coupled to the proximal threaded portion and a distal sled coupled to the distal threaded portion;

(c) at least one pair of anterior side plates comprising an anterior side top plate and an anterior side bottom plate, wherein the anterior side top plate is reversibly connected to the anterior side bottom plate and wherein each anterior side plate is discrete from, and oppose, each other; and (d) at least one pair of posterior side plates comprising a posterior side top plate and a posterior side bottom plate, wherein the posterior side top plate is reversibly connected to the posterior side bottom plate and wherein each posterior side plate is discrete from, and oppose, each other;

wherein when the center rod is rotated in a first rotation direction, the distal sled and the proximal sled move further apart relative to one another along the length of the center rod and wherein when the center rod is rotated in a second rotation direction opposite the first rotation direction the distal sled and the proximal sled move closer along the length of center rod; and preferably, wherein the expandable intervertebral spine implant is configured so that:

(i) when the distal sled and the proximal sled are positioned closest to each other within a central portion of the center rod, the implant is in a compact position;

(ii) when the distal sled and the proximal sled move farther apart along a first length in each direction from the center portion of the center rod, the anterior side plates and the posterior side plates move farther apart from one another and from the center rod thereby expanding the implant in a first expansion direction; and (iii) when the distal sled and the proximal sled move farther apart from the center portion along a second length of the center rod, the anterior side top plate and the anterior side bottom plate move apart from one another thereby expanding the implant on the anterior side in a second expansion direction.

Another aspect of the invention relates to methods of using the expandable intervertebral spine implants described herein. One embodiment of the invention relates to a method for stabilizing a spinal unit of a spinal column of a subject, the spinal unit comprising a superior vertebral bone, an inferior vertebral bone, an intervertebral disc space disposed there between, the method comprising:

(a) forming a skin incision in the subject;

(b) extending a tissue corridor from the skin incision to the intervertebral disc space;

(c) approaching the intervertebral disc space with the implants described herein using an insert tool, wherein the central rod is rotated and positioned so that the distal sled and the proximal sled are close to the central portion of the center rod thus reducing the dimensions of the implant for insertion;

(d) seating the implant within the intervertebral disc space using the insert tool;

(e) rotating the center rod using the insert tool to move the distal sled and the proximal sled farther apart along a first length from a center portion of the center rod and thus moving the anterior side plates and the posterior side plates farther apart from one another and from the center rod thereby expanding the implant in a first expansion direction;

(f) further rotating the center rod using the insert tool to move the distal sled and the proximal sled farther apart from a center portion along a second length of the center rod and thus move the anterior side top plate and the anterior side bottom plate apart from one another thereby expanding the implant on the anterior side in a second expansion direction; and (g) removing the insert tool.

Another aspect of the invention relates to methods of making and/or assembling the expandable intervertebral spine implants described herein and/or components thereof.

The foregoing has outlined some of the aspects of the present invention. These aspects should be construed strictly as illustrative of some of the more prominent features and applications of the invention, rather than as limitations on the invention. Many other beneficial results can be obtained by modifying the embodiments within the scope of the invention. Accordingly, for other objects and a full understanding of the invention, refer to the summary of the invention, the detailed description describing the preferred embodiment in addition to the scope of the invention defined by the claims and the accompanying drawings. The unique features characteristic of this invention and operation will be understood more easily with the description and drawings. It is to be understood that the drawings are for illustration and description only and do not define the limits of the invention.

BRIEF DESCRIPTION OF THE DRAWINGS

The above-mentioned and other features of the inventions disclosed herein are described below with reference to the drawings of the preferred embodiments. The illustrated embodiments are intended to illustrate, but not to limit the inventions. The drawings contain the following figures:

FIG. 13A is a perspective front side view of implant in a fully collapsed position for insertion. FIG. 13B is a perspective front side view of implant in a first intermediate expanded position. FIG. 13C is a perspective front side view of the implant in a fully expanded position.

DETAILED DESCRIPTION OF PREFERRED EMBODIMENTS

Figure 1:
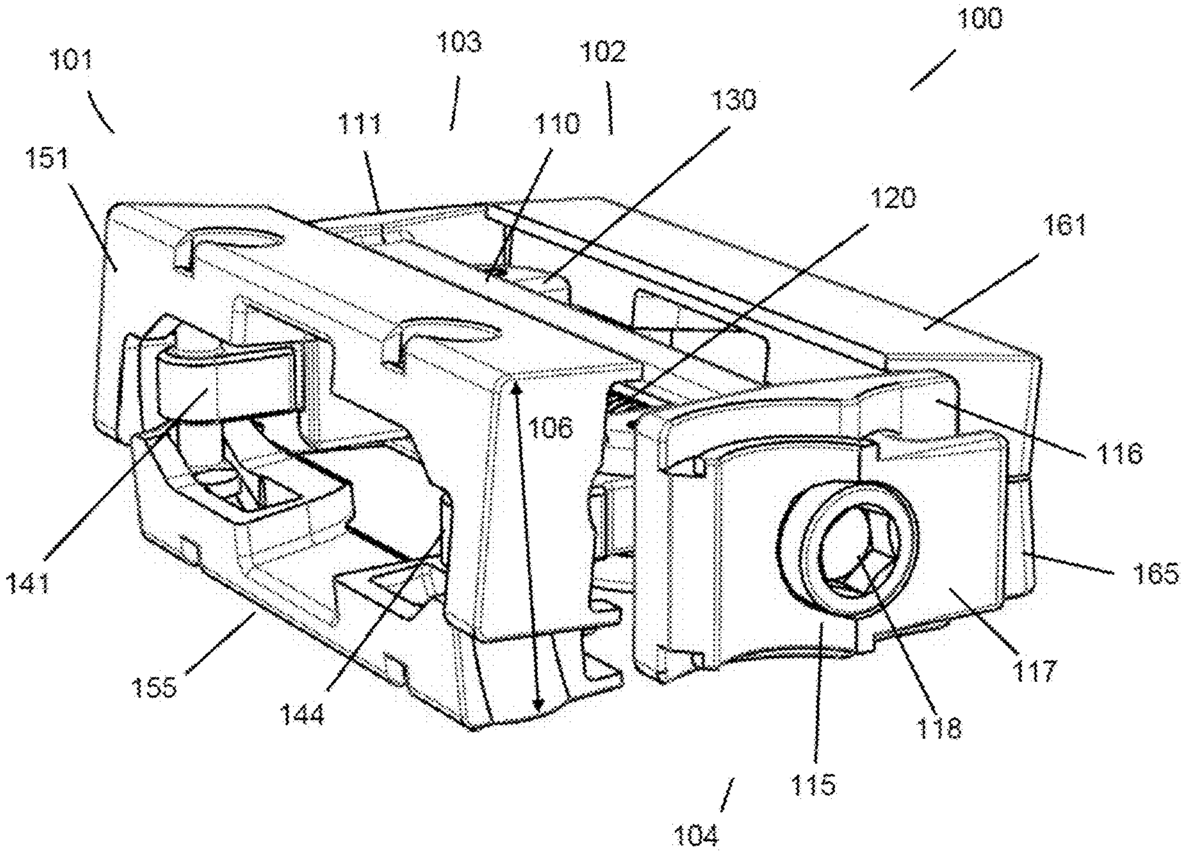
FIG. 1 is a perspective front side view of an expandable intervertebral spine implant according to one embodiment.

In the following description, for purposes of explanation, specific details are set forth in order to provide a thorough understanding of different aspects of the present invention. It will be evident, however, to one skilled in the art that the present invention as defined by the claims may include some or all of the features or embodiments herein described and may further include obvious modifications and equivalents of the features and concepts described herein.

DEFINITIONS

As used herein, the singular forms “a”, “an” and “the” include plural referents unless the context clearly dictates otherwise.

Ranges can be expressed herein as from “about” one particular value, and/or to “about” another particular value. When such a range is expressed, another aspect includes from the one particular value and/or to the other particular value. Similarly, when values are expressed as approximations, by use of the antecedent “about,” it will be understood that the particular value forms another aspect and “about” is utilized herein to represent an inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue. It will be further understood that the endpoints of each of the ranges are significant both in relation to the other endpoint, and independently of the other endpoint.

Terms used herein, such as “aspect” or “embodiment” or “exemplary” or “exemplified,” are not meant to show preference, but rather to explain that the aspect discussed thereafter is merely one example of the aspect presented.

Additionally, as used herein, relative terms, such as “substantially”, “generally”, “approximately”, and the like, are utilized herein to represent an inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

The term “connected to” includes connected directly or indirectly.

As used herein, the terms “optional” or “optionally” mean that the subsequently described event or circumstance may or may not occur or the component might be omitted, and that the description includes instances where the event or circumstance occurs and instances where it does not or when the component is present or not present.

The detailed description set forth below in connection with the appended drawings is intended as a description of presently-preferred embodiments of the invention and is not intended to represent the only forms in which the present invention may be constructed or utilized. The description sets forth the functions and the sequence of steps for constructing and operating the invention in connection with the illustrated embodiments. It is to be understood, however, that the same or equivalent functions and sequences may be accomplished by different embodiments that are also intended to be encompassed within the spirit and scope of the invention.

The invention relates to improved expandable intervertebral spine implants and methods of using the same and methods of making the same.

In the current field of orthopedic spine surgery, there currently is not an intervertebral spine implant that can be delivered through a posterolateral approach in a minimally invasive fashion, that also expands in width and angulation (restoring lordosis), as described herein. Other implants on the market that provide similar types of expansion and angulation features require the user to use approaches which are more invasive and time-consuming. The height expanding only or pre-angulated static implants on the market do not align their angulation to have the taller side sagittally balanced going from anterior to posterior of patient's midline, but instead enter the intervertebral disc space at the approximate 45 degree angle and continue their trajectory to have their taller side finish approximately 45 degrees off the midline contralaterally, thus attempting to restore disc height & sagittal balance by lifting/angulating off a corner and not the center.

The expandable intervertebral spine implants described herein provide improvements compared to prior implants.

Referring to the FIGS. 1-5, one aspect of the invention relates to an expandable intervertebral spine implant (100) having an anterior side (101), a posterior side (102), a distal end (103) and a proximal end (104), the implant comprising:

(a) a center rod (120) having a center rod length comprising a proximal threaded portion (122) having a proximal threading direction and a distal threaded portion (121) having a distal threading direction opposite the proximal threading direction;

(b) a proximal sled (132) coupled to the proximal threaded portion (122) and a distal sled (131) coupled to the distal threaded portion (121);

(c) at least one pair of anterior side plates comprising an anterior side top plate (151) and an anterior side bottom plate (155), wherein the anterior side top plate (151) is reversibly connected to the anterior side bottom plate (155) and wherein each anterior side plate (151/155) is discrete from, and oppose, each other; and (d) at least one pair of posterior side plates comprising a posterior side top plate (161) and a posterior side bottom plate (165), wherein the posterior side top plate (161) is reversibly connected to the posterior side bottom plate (165) and wherein each posterior side plate is discrete from, and oppose, each other;

(e) wherein when the center rod (120) is rotated in a first rotation direction, the distal sled (131) and the proximal sled (132) move further apart relative to one another along the length of the center rod (120) and wherein when the center rod (120) is rotated in a second rotation direction opposite the first rotation direction the distal sled (131) and the proximal sled (132) move closer along the length of center rod (120).

Figure 4:
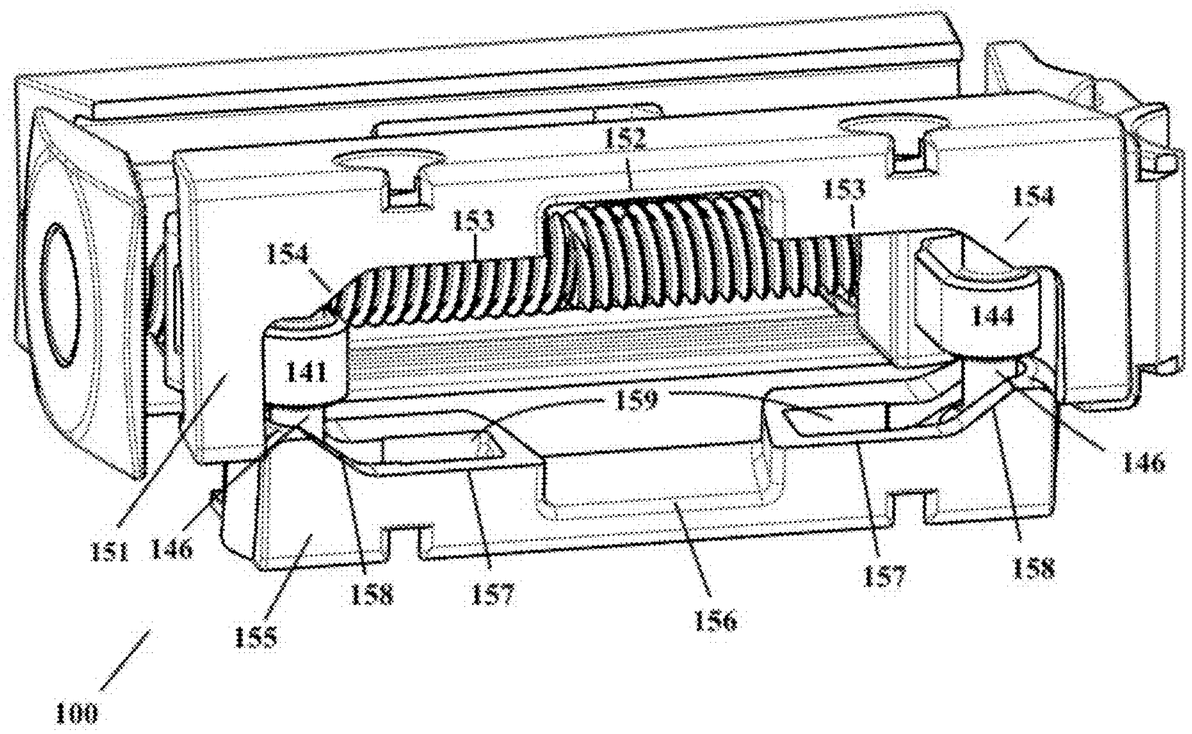
FIG. 4 is a perspective side view of the expandable intervertebral spine implant of FIG. 1 in a fully expanded position.

Preferably, the expandable intervertebral spine implant is configured so that:

(i) when the distal sled (131) and the proximal sled (132) are positioned closest to each other within a central portion of the center rod (120) (e.g., approximately the middle of the implant "length" (described below) from proximal to distal end), the implant is in a compact position (e.g., the implants smallest external dimensions to facilitate insertion into the intervertebral disc space);

(ii) when the distal sled (131) and the proximal sled (132) move farther apart along a first length in each direction from the center portion of the center rod (120), the anterior side plates (151/155) and the posterior side plates (161/165) move farther apart from one another and from the center rod (120) thereby expanding the implant in a first expansion direction (preferably, a direction approximately perpendicular to the implant length or the "width" (described below) of the implant from the external anterior side to the external posterior side); and (iii) when the distal sled (131) and the proximal sled (132) move farther apart from the center portion along a second length of the center rod (120), the anterior side top plate (151) and the anterior side bottom plate (155) move apart from one another thereby expanding the implant on the anterior side in a second expansion direction (preferably, approximately perpendicular to both the implant length and the implant width, that is the "height" of the implant on the anterior side is increased as shown in FIG. 4 showing anterior top side plate 151 is moved upwards and/or the anterior bottom plate 155 is moved downwards as shown).

According to preferred embodiments, the second expansion direction is approximately perpendicular to the first expansion direction, more preferably within 15 degrees of perpendicular, even more preferably within 10 degrees of perpendicular, even more preferably within 5 degrees of perpendicular, and most preferred within 2 degrees of perpendicular. Preferably, the first and second directions are determined or measured by the average direction of movement of the component. According to one preferred embodiment, the second expansion direction follows an arc starting directly perpendicular to the first expansion direction.

According to further preferred embodiments, the term "approximately perpendicular" means preferably within 15 degrees of perpendicular, more preferably within 10 degrees of perpendicular, even more preferably within 5 degrees of perpendicular, and most preferred within 2 degrees of perpendicular.

According to one embodiment, the distal sled (131) is connected (preferably reversibly connected) to anterior side distal articulating arm (141) and posterior side distal articulating arm (142).

According to another embodiment, the proximal sled (132) is connected (preferably reversibly connected) to anterior side proximal articulating arm (144) and posterior side proximal articulating arm (143).

According to preferred embodiments, the distal sled (131) is connected (preferably reversibly connected) to anterior side distal articulating arm (141) and posterior side distal articulating arm (142) and the proximal sled (132) is connected (preferably reversibly connected) to anterior side proximal articulating arm (144) and posterior side proximal articulating arm (143). Preferably, the anterior side distal articulating arm (141) and the anterior side proximal articulating arm (144) are configured to move the anterior side plates (151/155). Preferably, the posterior side distal articulating arm (142) and the posterior side proximal articulating arm (143) are configured to move the posterior side plates (161/165).

According to alternative embodiments, sleds (131/132) comprise components (e.g., internal prongs or other configurations) instead of separate articulating arms (141, 142, 143 and 144). For example, each sled (131/132) comprises an anterior side configuration and a posterior side configuration configured to move the anterior side plates (151/155) or posterior side plates (161/165).

Figure 12:
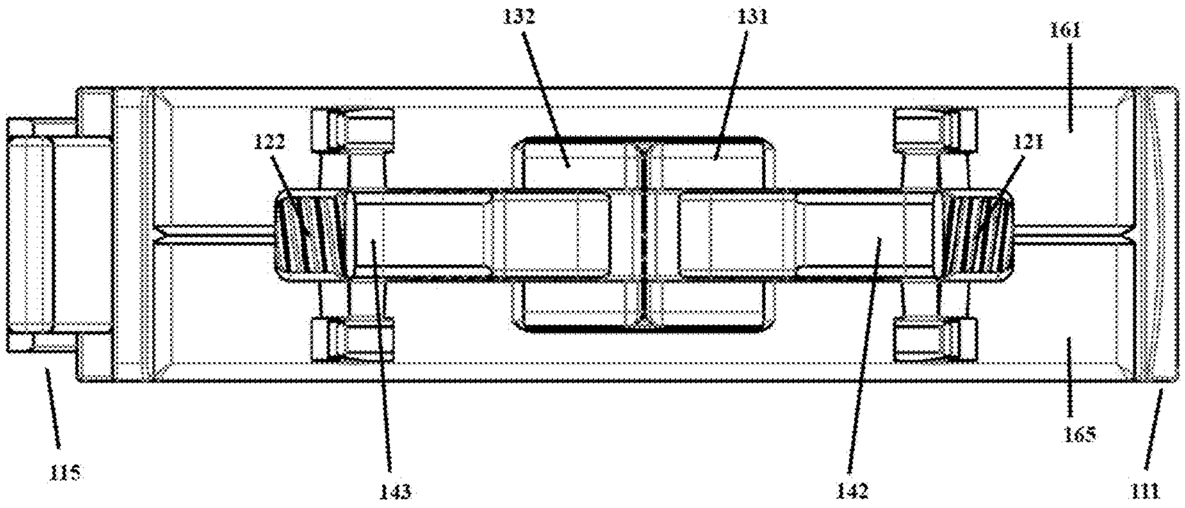
FIG. 12 is a side view of the posterior side of the expandable intervertebral spine implant of FIG. 1.

According to one embodiment, the same posterior side plate component is used for both posterior side plates (161/165) as shown in posterior side view of implant (100) shown in FIG. 12. Preferably, the posterior side plates (161/165) are configured opposite as shown in FIG. 12.

Figure 6:
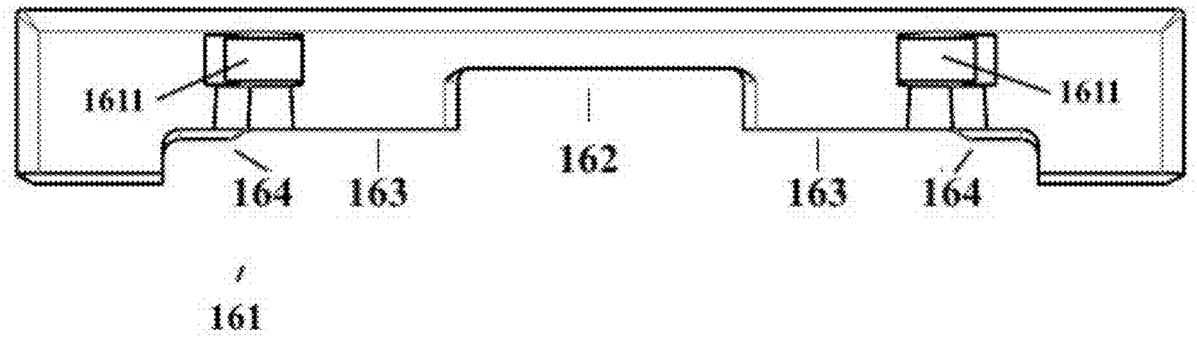
FIG. 6 is a side view of the posterior side top plate (161) of the expandable intervertebral spine implant of FIG. 1.
Figure 7:
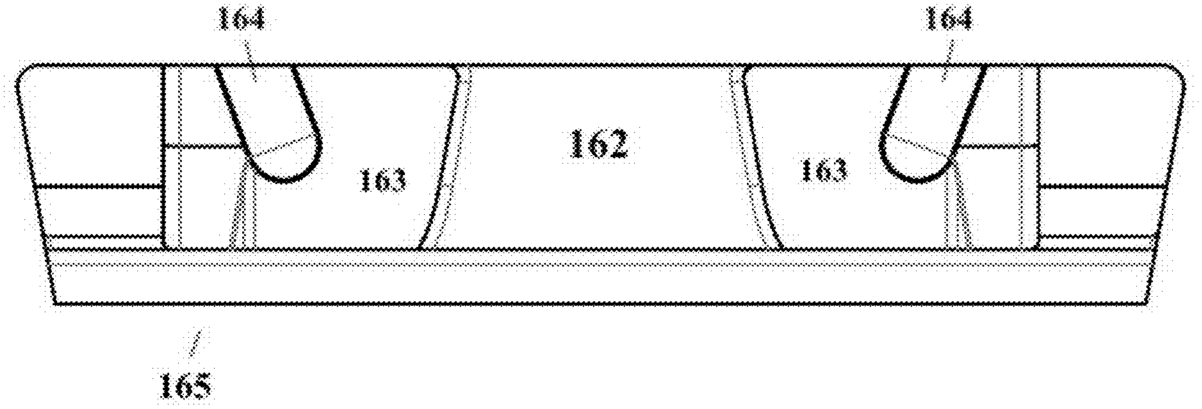
FIG. 7 is a top view of the posterior side bottom plate (165) of the expandable intervertebral spine implant of FIG. 1.

Preferably, each posterior side plate (161/165) comprises a flat horizontal central portion (162), a stepped-up portion (163) on each side of the flat horizontal central portion (162) and a ramping portion (164) on each end of the stepped-up portion (163) opposite the flat horizontal central portion (162), as shown in FIGS. 6, 7 and 12.

Figure 5:
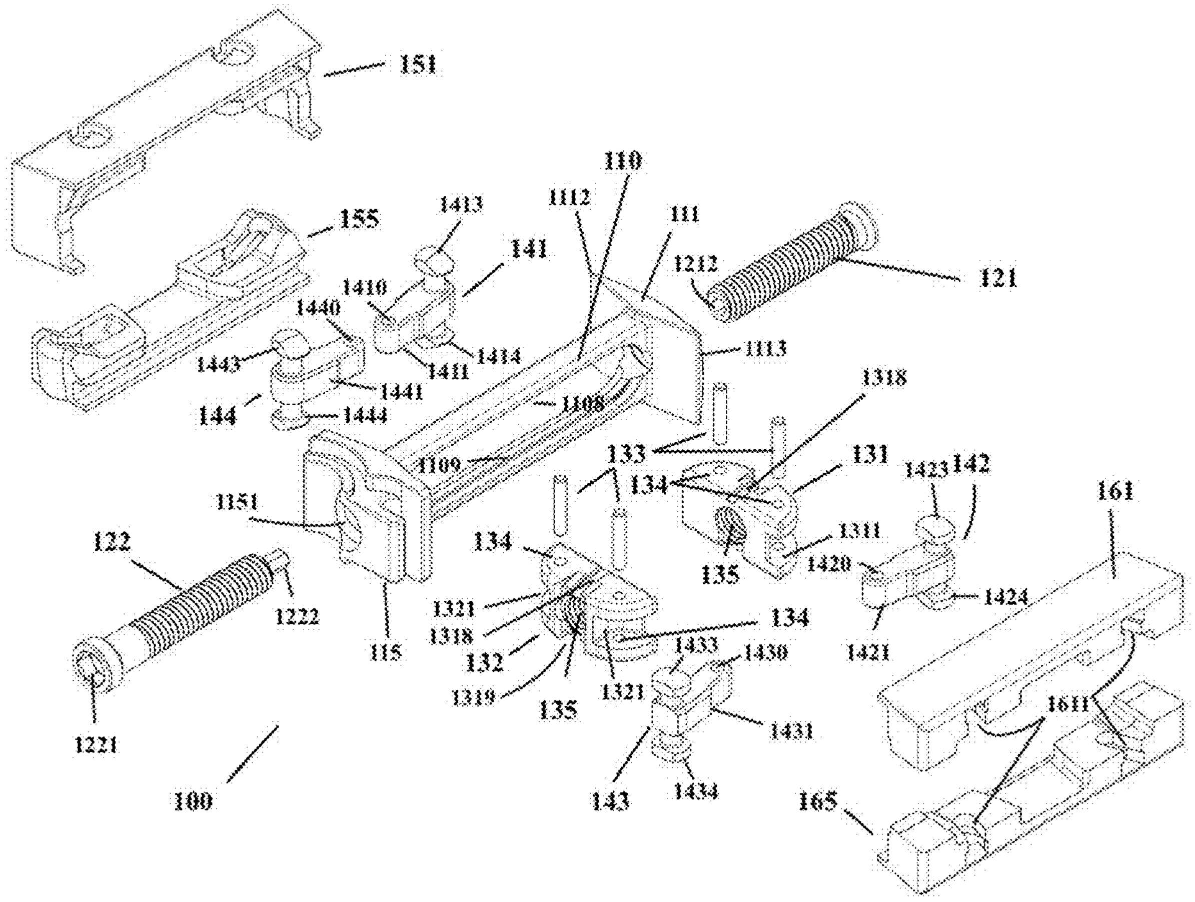
FIG. 5 is an exploded view of the expandable intervertebral spine implant of FIG. 1.

According to preferred embodiments, each posterior side plate (161/165) comprises at least one slot or opening (1611) configured to allow insertion of portion of posterior articulating arms (e.g., for facilitating assembly of implant) as shown in FIGS. 5 and 6, preferably the at least one slot or opening (1611) is on the posterior side of the posterior side plate (161/165). Preferably, the at least one slot or opening (1611) comprises at least two slot or openings (1611), at least one slot or opening (1611) located within the stepped-up portion (163) on each side of the flat horizontal central portion (162) as shown in FIGS. 5 and 6. Preferably, at least one slot or opening (1611) is "mushroom-shaped" as shown to facilitate insertion of portion of posterior articulating arms (e.g., for facilitating assembly of implant), for example, insert of "mushroom-shaped" prongs 1423/1424 of posterior articulating arm 142 and "mushroom-shaped" prongs 1433/1434 of posterior articulating arm 143.

According to another embodiment, the anterior side top plate (151) and the anterior side bottom plate (155) each have a U-shaped side profile as shown in FIGS. 8-11. Preferably, the U-shape of the anterior side top plate (151) is configured to reversibly slide into the U-shape of the anterior side bottom plate (155) forming an open space therebetween.

Figure 10:
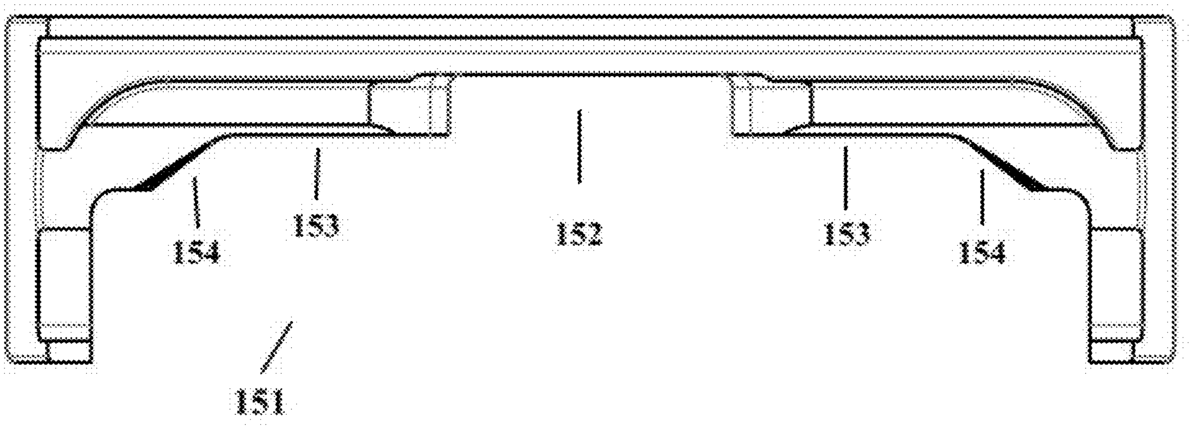
FIG. 10 is a side view of the anterior side top plate (151) of the expandable intervertebral spine implant of FIG. 1.
Figure 11:
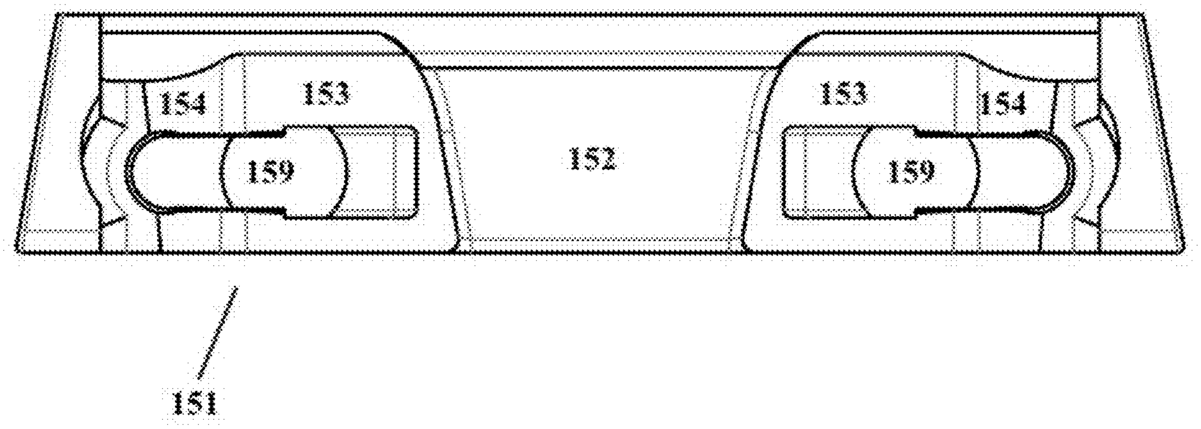
FIG. 11 is a top view of the anterior side top plate (151) of the expandable intervertebral spine implant of FIG. 1.

Preferably, the U-shape of the anterior side top plate (151) comprises a flat horizontal central portion (152), a stepped-up portion (153) on each side of the flat horizontal central portion (152) and a ramping portion (154) on each end or side of the stepped-up portions (153) opposite the flat horizontal central portion (see FIGS. 10 and 11).

Figure 8:
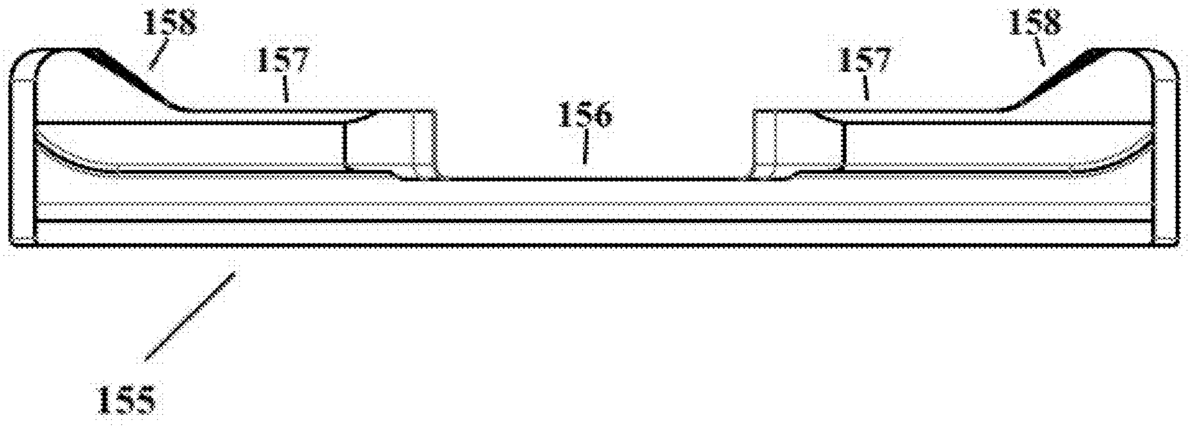
FIG. 8 is a side view of the anterior side bottom plate (155) of the expandable intervertebral spine implant of FIG. 1.
Figure 9:
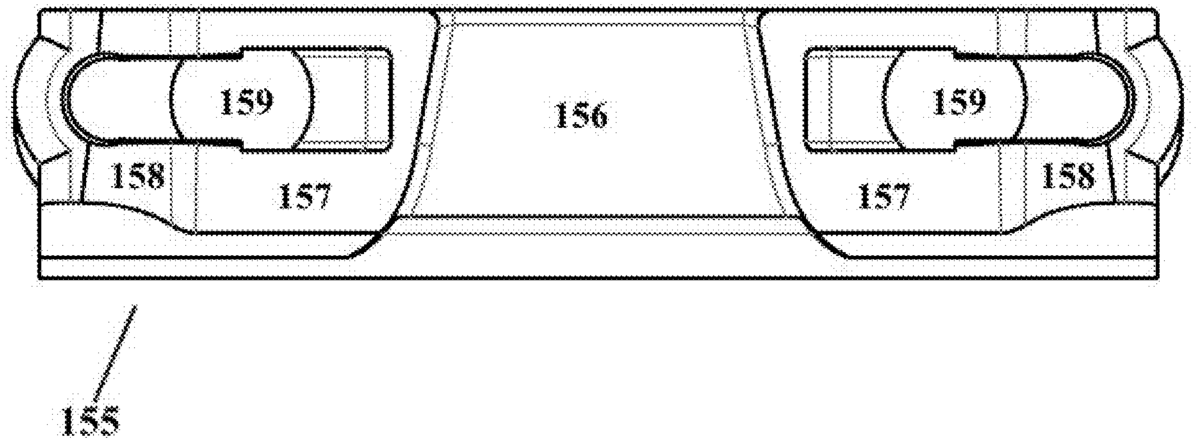
FIG. 9 is a top view of the anterior side bottom plate (155) of the expandable intervertebral spine implant of FIG. 1.

Preferably, the U-shape of the anterior side bottom plate (155) comprises a flat horizontal central portion (156), a stepped-up portion (157) on each side of the flat horizontal central portion (156) and an angled ramping portion (158) on each end of the stepped-up portion (157) opposite the flat horizontal central portion (156) (see FIGS. 8 and 9).

According to preferred embodiments, the U-shape of the anterior side top plate (151) and the U-shape of the anterior side bottom plate (155) are configured so that (a) when the pairs of opposing articulating arms (141/142 & 143/144) are positioned within the flat horizontal bottom of each anterior side plate (151/155) and the anterior side plates (151/155) and posterior side plates (161/165) are positioned closest to one another resulting in a compact implant for insertion; (b) when the pair of opposing articulating arms (141/142 & 143/144) are positioned within the step-up portion the anterior side plates (151/155) and the anterior side plates (151/155) and the posterior side plates (161/165) are positioned further apart from one another thus expanding the implant in a first direction; and (c) when the pair of opposing articulating arms (141/142 & 143/144) are positioned within the angled ramping portion of each anterior side plate (151/155), the anterior side top plate (151) and the anterior side bottom plate (155) are positioned still further apart from one another and thus expanding the implant in a second direction.

Preferably, the U-shape of the anterior side top plate (151) and the U-shape of the anterior side bottom plate (155) are configured so that when the pair of opposing articulating arms (141/142 & 143/144) are positioned within the angled ramping portion of each anterior side plate (151/155), the posterior side plates (161/165) are positioned closer to the center rod (120).

Preferably, the U-shape of the anterior side top plate (151) and the U-shape of the anterior side bottom plate (155) are configured so that when the pair of opposing articulating arms (141/142 & 143/144) are positioned within the angled ramping portion of each anterior side plate (151/155), the posterior side plate (161) and posterior side plate (165) are rotated relative to each other.

According to another embodiment, the implant has dimensions and configuration adapted to allow the implant to be inserted into an intervertebral disc space via Kambin's Triangle, as described below.

Figure 3:
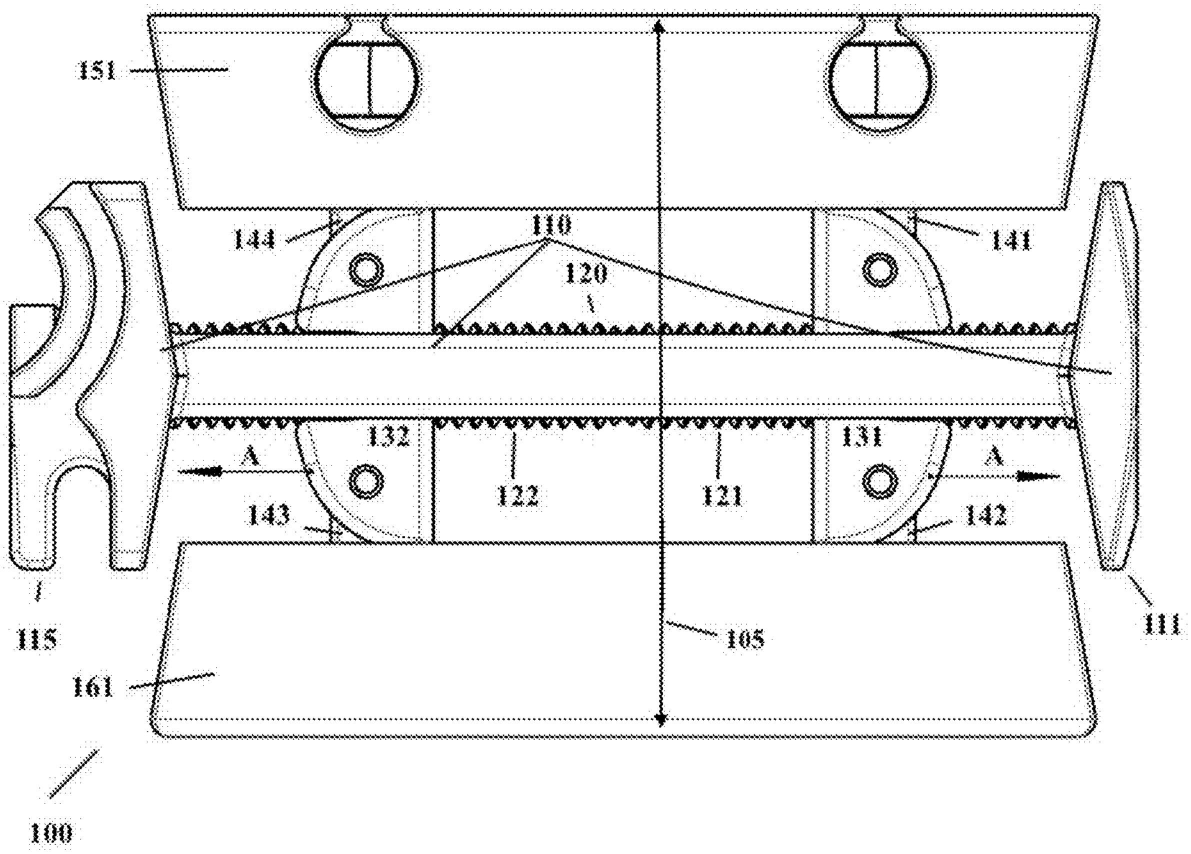
FIG. 3 is a top view of the expandable intervertebral spine implant of FIG. 1 in an intermediate expanded position.

Preferably, the implant (100) comprises an adjustable width (105) (e.g., as shown in FIG. 3) and adjustable height (106) (e.g., as shown in FIG. 1). According to one embodiment, the largest width and/or largest height of implant (100) is measured as the width (105)/height (106).

According to alternate embodiments, the length of the implant (e.g., measured from proximal surface of frame (110) to distal surface) by including a means for increasing the length of the frame (110)/implant (100), for example, at least one component at the end of frame (110) (insertion component (111) or frame proximal end (115)) includes an opening with a threaded ring configured to fit within the opening and configured to fit around a threaded end of center rod (120) and be rotated within the opening to move the component (111/115) along the length of the center rod (120).

Preferably, the external dimensions of the "compact" implant (e.g., FIG. 13A) comprises (i) a length of 20 to 40 mm, preferably 28 to 32 mm, (ii) a width of 5 to 15 mm, preferably 8 to 11 mm and/or (iii) a height of 4 to 10 mm, preferably 6 to 8 mm.

Preferably, the external dimensions of the "intermediate expanded" implant (FIG. 13B) comprises (i) a length of 20 to 40 mm, preferably 28 to 32 mm, (ii) a width of 12 to 25 mm, preferably 17 to 20 mm and/or (iii) a height of 4 to 10 mm, preferably 6 to 8 mm.

Preferably, the external dimensions of the "fully expanded" implant (FIG. 13C) comprises (i) a length of 20 to 40 mm, preferably 28 to 32 mm, (ii) a width of 12 to 25 mm, preferably 17 to 20 mm and/or (iii) a height of 6 to 20 mm, preferably 11 to 14 mm.

According to preferred embodiments, the implant further comprises a frame (110) that couples to and contains the center rod (120), the distal sled (131) and the proximal sled (132). Preferably, the frame (110) comprises a frame distal end having an insertion component (111) configured to facilitate insertion of the implant. Preferably, the insertion component (111) is configured to form a T-shape with frame (110). Preferably, the insertion component (111) comprises an anterior edge (1112) and a posterior edge (1113). Preferably, the frame (110) comprises a frame proximal end (115) including a socket or opening (1151) configured for receipt of an insert tool to rotate the center rod (120). According to one preferred embodiment, frame (110) integrally comprises frame proximal end (115) and insertion component (111) (e.g., a single molded frame (110) including configured ends (111/115).

According to another embodiment, the proximal threaded portion (122) of center rod (120) comprises a proximal end (1221) and a distal end (1222), wherein the proximal end (1221) comprises a recess configured for receipt of the insert tool (not shown) to rotate the center rod (120) and the distal end (1222) comprises a prong configuration to connect (either reversibly or permanently connect, preferably permanently) to the distal threaded portion (121) (or vice versa with the distal threaded portion (121) comprising a prong and the distal end of the proximal threaded portion (122) comprising a recess or socket configured for receipt of the prong). According to preferred embodiments, the prong-recess configuration comprises a hex socket, bevel gear or other means for connecting and/or rotating and/or manipulating the components, preferably a bevel gear configuration.

Preferably, the distal threaded portion (121) of center rod (120) comprises a proximal end (1212) which comprises a recess configured for receipt of the prong configuration of distal end (1222) of the proximal threaded portion (122) of center rod (120).

According to preferred embodiments, each sled (131/132) comprises a through-hole (135) for center rod (120), as shown in FIG. 5.

According to preferred embodiments, each sled (131/132) comprises a pair of through-holes (134) on each side of the sled for insertion of pin (133), as shown in FIG. 5.

According to preferred embodiments, each sled (131/132) comprises a side recess (1311/1321) configured for receipt of portion of articulating arms. Preferably, each side recess (1311/1321) comprises the pair of aligned through-holes (134), as shown in FIG. 5.

According to preferred embodiments, each sled (131/132) comprises a top central channel (1318) and/or bottom central channel (1319) configured to accommodate a top rail (1108) and/or bottom rail (1109) of frame (110), as shown in FIG. 5.

According to another embodiment, each articulating arm (141/142 and 143/144) comprises at least one through-hole (1410/1420 and 1430/1440) for insertion of the pins (133) to connect the articulating arm (141/142 and 143/144) to the corresponding sleds (131/132).

According to another embodiment, each articulating arm (141/142 and 143/144) comprises a connector component (1411/1421 and 1431/1441) comprising the at least one through-hole and at least one knob component (1413/1423 and 1433/1443).

According to another embodiment, each articulating arm (141/142 and 143/144) comprises a connector component (1411/1421 and 1431/1441) comprising the at least one through-hole and at least one top knob component (1413/1423 and 1433/1443) and at least one bottom knob component (1414/1424 and 1434/1444). Preferably, the at least one top knob component (1413/1423 and 1433/1443) and at least one bottom knob component (1414/1424 and 1434/1444) are each approximately perpendicular to corresponding connector component (1411/1421 and 1431/1441) and approximately oriented in opposite direction.

According to another embodiment, each articulating arm (141/142 and 143/144) comprises at least one knob component (1413/1423 and 1433/1443) configured for moving at least one side plate (e.g. anterior side plates (151/155) and the posterior side plates (161/165)). Preferably, each side plate (e.g. anterior side plates (151/155) and the posterior side plates (161/165)) comprise a channel along the step-up portion and ramped portion of each side plate to accommodate one knob component (1413/1423 and 1433/1443).

Preferably, each knob component is mushroom-shaped, as shown in FIG. 5.

Preferably, each sled (131/132) comprises at least one side recess (1311/1321) for insertion of at least a portion of the connector component (1411/1421 and 1431/1441) of each articulating arm (141/142 and 143/144).

According to preferred embodiments, the frame proximal end (115) comprises an opening (1151) configured to allow an insert tool to secure and pivot the implant within an intervertebral disc space and also to contact and rotate the proximal end of the center rod (120).

Another embodiment relates to an expandable intervertebral spine implant having an anterior side, a posterior side, a distal end and a proximal end, the implant comprising:

(a) a center support means having a center rod length comprising a proximal threaded portion having a proximal threading direction and a distal threaded portion having a distal threading direction opposite the proximal threading direction;

(b) a proximal sledding means coupled to the proximal threaded portion and a distal sledding means coupled to the distal threaded portion;

(c) at least one pair of anterior side plates comprising an anterior side top plate and an anterior side bottom plate, wherein the anterior side top plate is reversibly connected to the anterior side bottom plate and wherein each anterior side plate is discrete from, and oppose, each other; and (d) at least one pair of posterior side plates comprising a posterior side top plate and a posterior side bottom plate, wherein the posterior side top plate is reversibly connected to the posterior side bottom plate and wherein each posterior side plate is discrete from, and oppose, each other;

wherein when the center support means is rotated in a first rotation direction, the distal sledding means and the proximal sledding means move further apart relative to one another along the length of the center support means and wherein when the center support means is rotated in a second rotation direction opposite the first rotation direction the distal sledding means and the proximal sledding means move closer along the length of center support means; and preferably, wherein the expandable intervertebral spine implant is configured so that:

(i) when the distal sledding means and the proximal sledding means are positioned closest to each other within a central portion of the center support means, the implant is in a compact position;

(ii) when the distal sledding means and the proximal sledding means move farther apart along a first length in each direction from the center portion of the center support means, the anterior side plates and the posterior side plates move farther apart from one another and from the center support means thereby expanding the implant in a first expansion direction; and (iii) when the distal sledding means and the proximal sledding means move farther apart from the center portion along a second length of the center support means, the anterior side top plate and the anterior side bottom plate move apart from one another thereby expanding the implant on the anterior side in a second expansion direction.

Another aspect of the invention relates to method of using the implants defined above, preferably a method comprising insertion of the implant into an intervertebral disc space.

According to one embodiment, users (e.g., doctors) will first prepare the intervertebral disc, similar to other procedures, preferably through a provided minimally invasive cannula. Once the disc space is prepped, the implant will be inserted through the cannula, preferably through Kambin's Triangle or other natural opening, and into the intended intervertebral disc space. Once in the disc space, an insertion tool device (not shown) will articulate the implant into the desired position and orientation, preferably parallel to the medial-lateral (coronal) plane. Once articulated into position, the insertion tool device will be used to interact with the implant device, expanding it in overall footprint (preferably expanding the width and height of the implant) and expanding it in angulation (see FIGS. 1 and 13A-C).

Another embodiment of the invention relates to a method for stabilizing a spinal unit of a spinal column of a subject, the spinal unit comprising a superior vertebral bone, an inferior vertebral bone, an intervertebral disc space disposed there between, the method comprising:

(a) forming a skin incision in the subject;

(b) extending a tissue corridor from the skin incision to the intervertebral disc space;

(c) approaching the intervertebral disc space with the implant using an insert tool, wherein the central rod (120) is rotated and positioned so that the distal sled (131) and the proximal sled (132) are close to the central portion of the center rod (120) thus reducing the dimensions of the implant for insertion;

(d) seating the implant within the intervertebral disc space using the insert tool;

(e) rotating the center rod (120) using the insert tool to move the distal sled (131) and the proximal sled (132) farther apart along a first length from a center portion of the center rod (120) and thus moving the anterior side plates (151/155) and the posterior side plates (161/165) farther apart from one another and from the center rod (120) thereby expanding the implant in a first expansion direction;

(f) further rotating the center rod (120) using the insert tool to move the distal sled (131) and the proximal sled (132) farther apart from a center portion along a second length of the center rod (120) and thus move the anterior side top plate (151) and the anterior side bottom plate (155) apart from one another thereby expanding the implant on the anterior side in a second expansion direction; and (g) removing the insert tool.

Figure 13A:
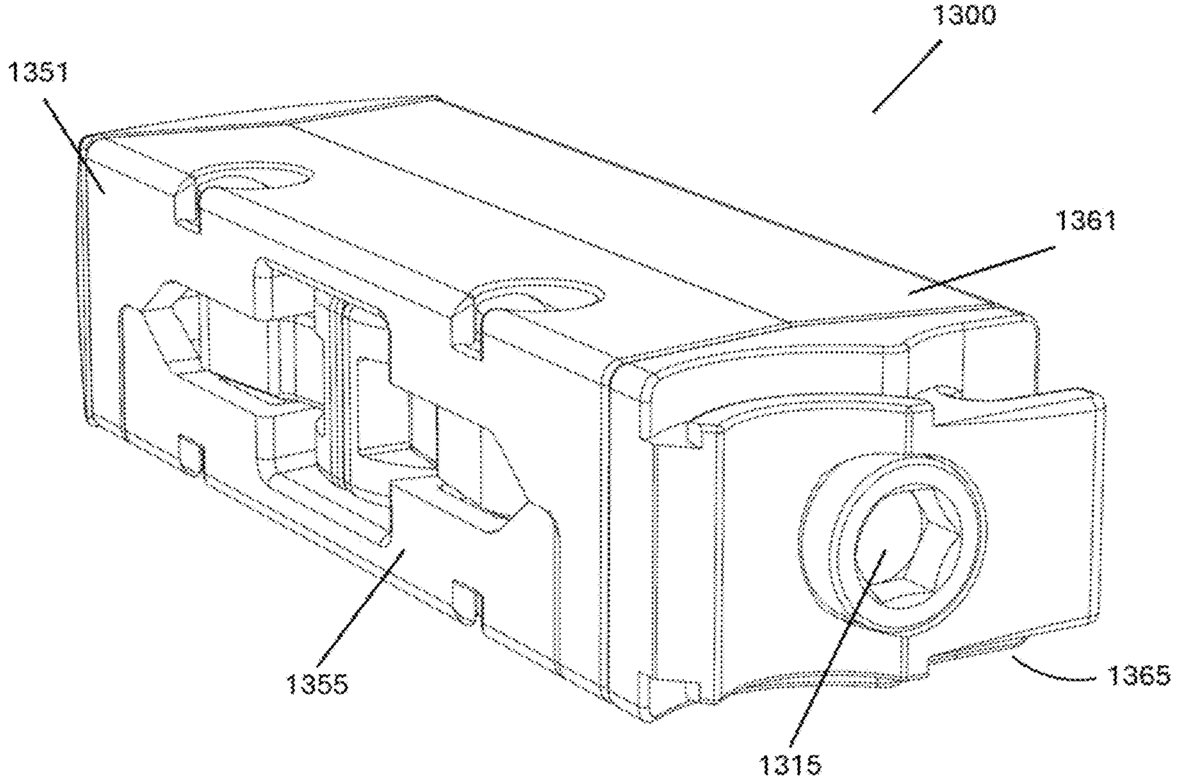
FIGS. 13A-C are perspective front side views of an expandable intervertebral spine implant according to another embodiment.
Figure 13B:
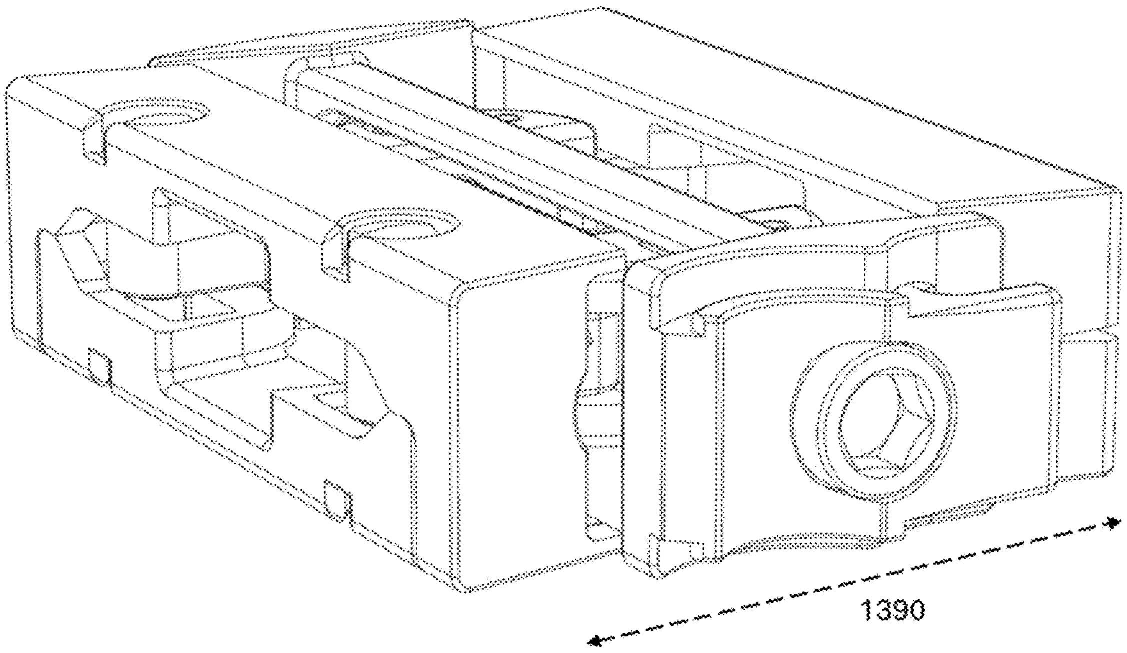
Figure 13C:
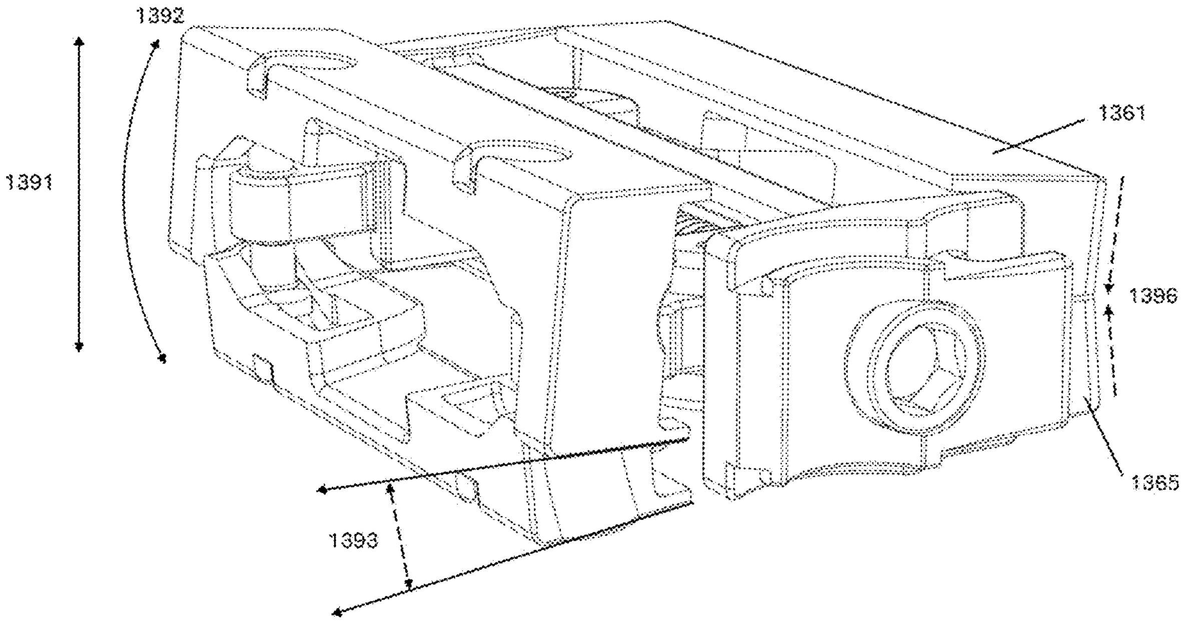

FIGS. 13A-C show the preferred expansion/angulation steps for use of an implant according to one preferred embodiment of the invention.

FIG. 13A shows implant 1300 in a compact position including anterior side plates (1351/1355) adjacent to posterior side plates (1361/1365), preferably each internal edge of anterior side plates (1351/1355) and posterior side plates (1361/1365) are in contact or approximately close to contact as shown. FIG. 13A shows implant (1300) in a compact position with its smallest overall external dimensions (preferably smallest width and height) to allow the compact implant (1300) to be inserted into the intervertebral disc space with the smallest skin incision and/or narrowest tissue corridor and/or advantageously compact to facilitate manipulating and/or orienting the implant within the intervertebral disc space to allow for accurate placement and positioning of the implant within the intervertebral disc space.

FIG. 13B shows the implant (1300) intermediately expanded along a first direction (1390) where anterior side plates (1351/1355) and posterior side plate (1361/1365) are moved apart from each other and/or also preferably each moved away from the center rod, preferably to increase the "width" of the implant.

FIG. 13C shows implant (1300) fully expanded (e.g., sleds fully separated on the center rod) wherein anterior side plates (1351/1355) are moved apart from one another, preferably anterior side plates (1351/1355) are moved apart in an arc (1392) so the top surface of anterior side top plate (1351) and bottom surface of anterior side bottom plate (1355) are eventually angled relative to each other (as shown) to provide the anterior side of implant (1300) with angulation to improve the fit of the implant within the intervertebral disc space.

Preferably, posterior side plates (1361/1365) are moved tighter together (e.g., as shown as direction 1396 in FIG. 13C) when the sleds are fully separated on the center rod to allow the expansion on the anterior side. That is, anterior side plates (1351/1355) are moved apart from one another, the posterior side plates (1361/1365) are pulled closer to each other and/or closer to the center rod. Preferably, the top surface of posterior top plate (1361) is angled relative to the bottom surface of posterior bottom plate (1365) as shown in FIG. 13C.

According to a preferred embodiment, the method further comprises, after the step of seating the implant in the intervertebral disc space, pivoting the implant within the intervertebral disc space. As described above, the compact implant facilitates manipulating and/or orienting the compact implant within the intervertebral disc space to allow for accurate placement of the implant. According to preferred embodiments, the requirement and magnitude of this manipulation/orientation step is dependent on the specific approach for approaching the intervertebral disc space and/or the access angle to the spine, specifically the intervertebral disc space. According to particularly preferred embodiments, this step is required and implemented for the Kambin's Triangle approach or other natural opening approach described below.

According to another preferred embodiment, the intervertebral disc space comprises an anterior side, the spinal column of the subject comprises a coronal plane, and the center rod (120) comprises a longitudinal axis and further comprising, after the seating of the implant in the intervertebral disc space, pivoting the implant within the intervertebral disc space such that the anterior side plates (151/155) are predominantly positioned along the anterior side of the intervertebral disc space and the longitudinal axis of the center rod (120) is approximately parallel to the coronal plane of the subject.

Another embodiment of the invention relates to a method for stabilizing a spinal unit of a spinal column of a subject, the spinal unit comprising a superior vertebral bone, an inferior vertebral bone, an intervertebral disc space disposed there between, and a Kambin's triangle formed by the superior endplate of the inferior vertebral bone, superior articular process of the inferior vertebral bone and a path of a spinal nerve and a first vertical axis that extends, in a cephalad to caudad direction, along a vertical plane of the spinal column, the method comprising:

(a) forming a skin incision in the subject;

(b) extending a tissue corridor from the skin incision through the Kambin's triangle using a cannula;

(c) approaching the intervertebral disc space with the implant via the cannula using an insert tool, wherein the central rod (120) is rotated so that the distal sled (131) and the proximal sled (132) are close to the central portion of the center rod (120) thus reducing the dimensions of the implant for insertion;

(d) seating the implant within the intervertebral disc space using the insert tool;

(e) rotating the center rod (120) using the insert tool to move the distal sled (131) and the proximal sled (132) farther apart along a first length from a center portion of the center rod (120) and thus moving the anterior side plates (151/155) and the posterior side plates (161/165) farther apart from one another and from the center rod (120) thereby expanding the implant in a first expansion direction;

(f) further rotating the center rod (120) using the insert tool to move the distal sled (131) and the proximal sled (132) farther apart from a center portion along a second length of the center rod (120) and thus move the anterior side top plate (151) and the anterior side bottom plate (155) apart from one another thereby expanding the implant on the anterior side in a second expansion direction; and (g) removing the insert tool.

According to a preferred embodiment, the method further comprises, after the step of seating the implant in the intervertebral disc space, pivoting the implant within the intervertebral disc space.

According to another preferred embodiment, the intervertebral disc space comprises an anterior side, the spinal column of the subject comprises a coronal plane, and the center rod (120) comprises a longitudinal axis and further comprising, after the seating of the implant in the intervertebral disc space, pivoting the implant within the intervertebral disc space such that the anterior side plates (151/155) are predominantly positioned along the anterior side of the intervertebral disc space and the longitudinal axis of the center rod (120) is approximately parallel to the coronal plane of the subject.

Preferably, the method further comprises pivoting the implant within the intervertebral disc space such that the anterior side plates (151/155) are predominantly positioned along the anterior side of the intervertebral disc space, such that the longitudinal axis of the center rod (120) is approximately parallel to the patient's coronal plane. The requirement and magnitude of this step is dependent on the specific approach or access angle to the spine. This step would be required for the Kambin's Triangle approach.

According to preferred embodiments, the implants described herein allow the user to deliver it to the patient via an endoscopic oblique lateral approach approximately 45 degrees off midline, through Kambin's Triangle, providing a very minimally invasive approach for surgeons and their patients. This procedure results in less blood loss, less radiation exposure, increased bony anatomy preservation, and faster procedure (less than half the time) allowing more patients to be treated. Once delivered to the intervertebral disc space, the implants described herein are configured to be maneuvered to align parallel with the patient's medial-lateral (coronal) plane and expand outwards in footprint (width) and in height asymmetrically (angulation).

Figure 2:
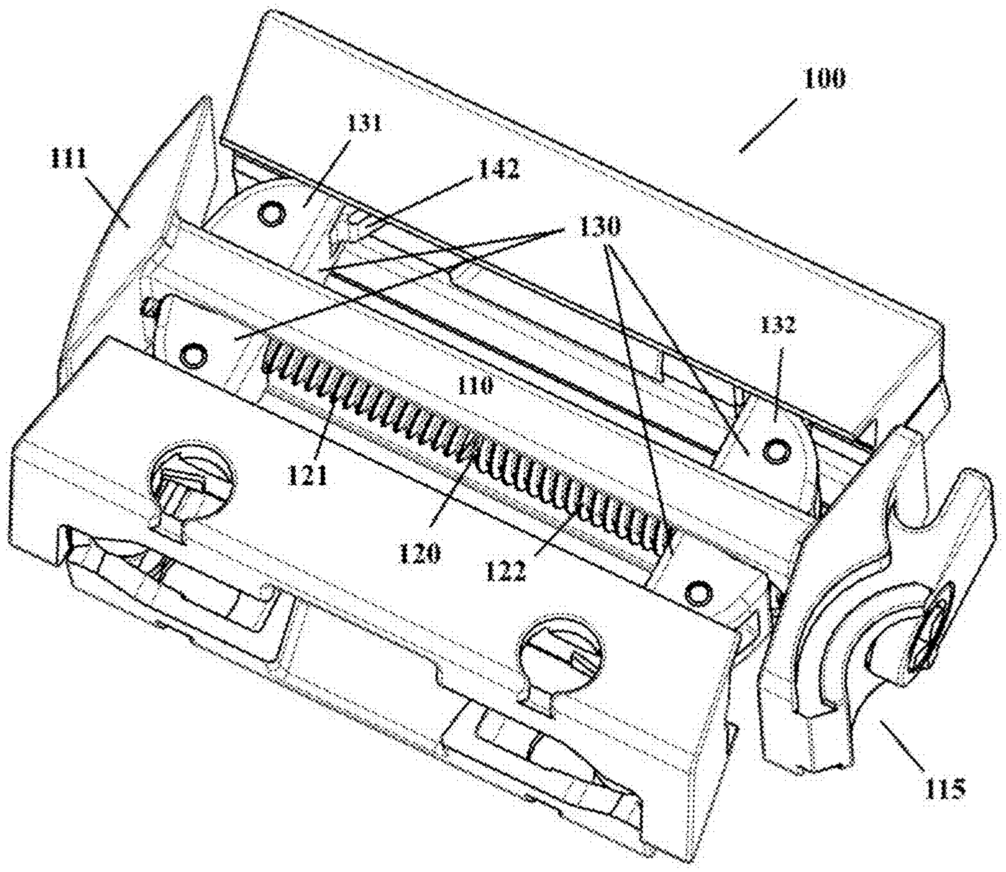
FIG. 2 is a perspective top view of the expandable intervertebral spine implant of FIG. 1 in a fully expanded position.

The inventive design is such that it will allow the users to adjust the angulation of the device to best fit the required Anterior-Posterior restoration required for the patient. As described herein, referring to FIGS. 1 and 2, the expansion of the implant device (100) is preferably controlled and actuated by at least two opposing sleds (131/132) which are coupled to a threaded center rod (120). The threaded rod (120) and two opposing sleds (131/132) are both coupled and contained by a frame (110). The insertion device (not shown) will interact with the threaded rod (120), by turning or rotating it. As the threaded rod (120) is turned, the two sleds (131/132) are forced in opposite directions, to the outward portion of the implant (100) (FIGS. 1 and 2). Coupled to each of the sleds (131/132) are two articulating arms as shown in FIG. 3 (arms 141/142 coupled to sled 131 and arms 143/144 coupled to sled 132). As the sleds (131/132) travel in opposite directions (as shown by arrows in FIG. 3), each of the articulating arms (preferably two on each sled; preferably four in total) are forced to hinge open anterior side plates (151/155) and posterior side plates (161/165) away from the centerline of the implant (100) (as shown in FIG. 2). This action is the mechanism that results in an intermediate expanded footprint and/or increased overall dimensions of the implant (100) in a first direction, preferably anterior side plates (151/155) and posterior side plates (161/165) moving away from each other in the first direction. As the threaded rod (120) continues to be turned, at a certain point in the expansion the sleds (131/132) begin to push the anterior side arms (151/155) in a linear fashion causing them to ramp open the anterior side plates, preferably anterior top plate (151) moving away from anterior bottom plate (155) (See, FIG. 4). Preferably, the ramping action provides the mechanism that results in the adjustable angulation of the implant. Once the implant has been positioned and expanded as desired, the surgeon will detach the insertion device from the implant and complete the remainder of the procedure as required.

Another aspect of the invention relates to method of making the implants defined above. According to one embodiment, the implant is constructed from Titanium and/or Titanium alloys such as Ti-6Al4V ELI.

According to preferred embodiments, some of the components of the implant are made through additive manufacturing via Direct Metal Laser Sintering (DMLS) on a powder bed fusion machine. Preferably, the components that are additively manufactured may leverage patterned latticed volumes to exhibit a range of porosities. According to preferred embodiments, other components are manufactured via traditional subtractive manufacturing of Mill or Lathe machining.

Preferably the implant is preferably assembled, and preferably tested, before ready for use. According to one embodiment, the implant is assembled by an assembly method comprising:

(a) inserting sleds (131/132) into frame (110) between upper rail (1108) and lower rail (1109) and, preferably clipped in between rails (1108/1109) aligned with upper channels (1318) and bottom channels (1319);

(b) threading the proximal threaded portion (122) through opening (1151) at proximal end (115) of frame (110) and through opening (135) of proximal sled (132);

(c) threading distal threaded portion (121) through a distal opening at distal end (111) of frame (110) and through opening (135) of distal sled (131);

(d) connecting the proximal threaded portion (122) to the distal threaded portion (121) forming center rod (120) supporting sleds (131/132) within frame (110);

(e) attaching each posterior side plates (161/165) to frame (110) using articulating arms (142/143);

(f) attaching each anterior side plates (151/1155) to frame (110) using articulating arms (141/144); and (g) attaching articulating arms (141/142) to sled (131) and articulating arms (143/144) to sled 132, and preferably securing the same using pins (133) through sled holes (134) and articulating arms holes (1410, 1420, 1430 and 1440).

Preferably, the method further comprises rotating center rod (120) to further compact implant before use.

Preferably, the method further comprises rotating center rod (120) in both directions to confirm implant is properly assembled for expansion and/or angulation and, preferably further rotating to fully compact the implant for insertion.

Another aspect of the invention relates to insert tools configured for inserting and pivoting the implant and expanding the implant by rotating the center rod as described above.

Figure 14:
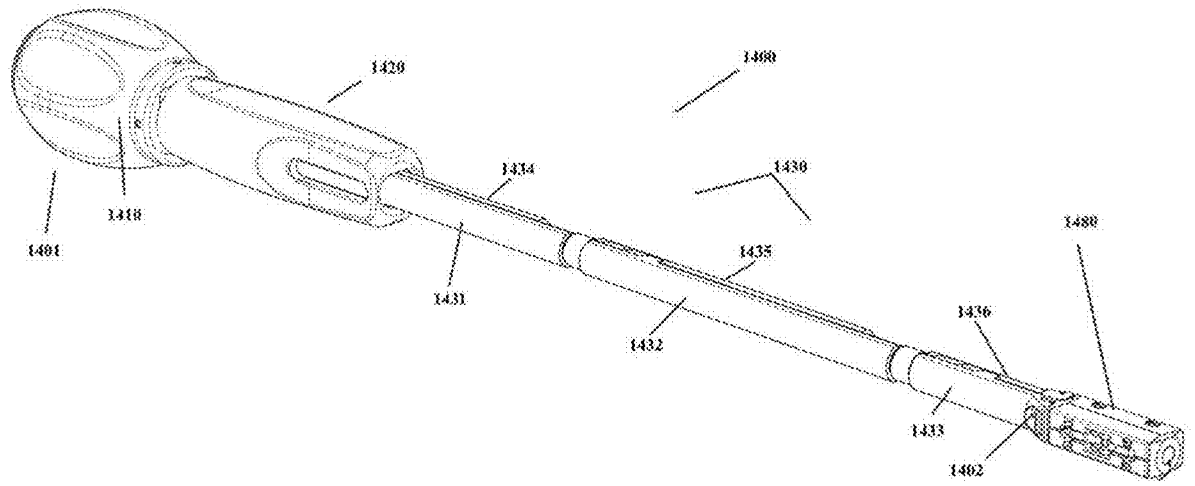
FIG. 14 is a perspective view of an insert tool connected to an implant according to one embodiment of the invention.
Figure 15A:
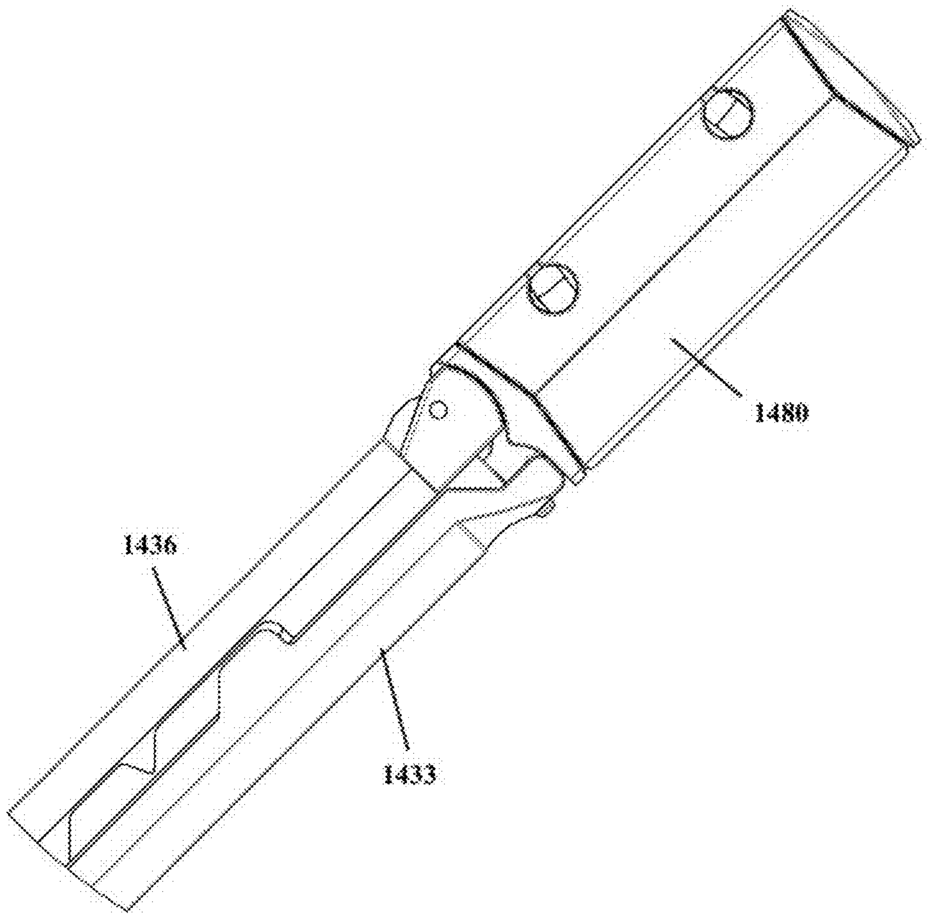
FIG. 15A shows the insert tool of FIG. 14 reversibly connected to the implant prior to articulation of the tool.
Figure 15B:
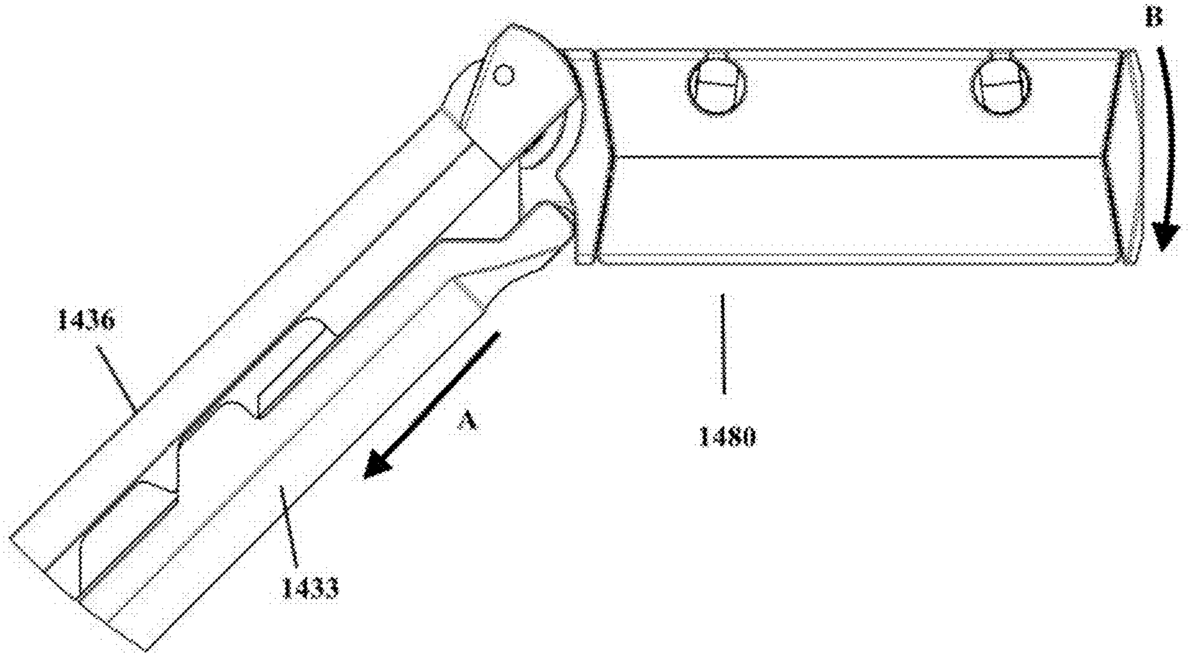
FIG. 15B shows the insert tool of FIG. 14 after articulation of the tool showing the pivot of the implant.

FIG. 14 shows an insert tool 1400 reversibly connected to implant 1480 according to one embodiment of the invention. Insert tool 1400 has a proximal end 1401 and a distal end 1402 connected to implant 1480. Insert tool 1400 comprises a rotatable knob 1410 at proximal end 1401 and grip 1420 adjacent to rotatable knob 1410. Insert tool 1400 further comprises insert shaft 1430 comprising two shaft arms including right arm 1431/1432/1433 and left arm 1434/1435/1436. FIG. 14 shows right arm and left arm of insert shaft 1430 as three segments (right arm 1431/1432/1433 and left arm 1434/1435/1436) as a preferred embodiment but alternative designs can be used (e.g., two segments, four segments or no segments (single shaft for each right and left arms)). Insert shaft 1430 is connected to rotatable knob 1410 via an opening within grip 1420, as shown, allowing insert shaft 1430 to be manipulated within grip 1420. Each of right arm 1431/1432/1433 and left arm 1434/1435/1436 are configured to interact with the back/proximal end of the frame of implant 1480 as shown in FIGS. 15A-B. The insert tool 1400 is configured so that right arm 1431/1432/1433 is translated (shown as arrow "A" in FIG. 15B) relative to left arm 1434/1435/1436 by rotating the rotatable knob 1410, which forces the entire implant 1480 to pivot (as shown as pivot arrow "B" in FIG. 15B). Insert shaft 1430 (including right arm 1431/1432/1433 and left arm 1434/1435/1436) comprises a channel hole (not shown) through the shaft 1430 center to allow a driver tool (not shown) to be inserted through the channel hole and engage the center rod of the implant 1480 to start the expansion of the implant after implantation into the intervertebral disc space. Preferably, the entire insert tool 1400 including rotatable knob 1410 includes channel hole for insertion of the driver tool. Alternatively, rotatable knob 1410 and grip 1420 are detached from shaft 1430 prior to insertion of driver tool. Rotatable knob 1410 is also configured to release the insert tool 1400 from the implant by continuing to rotate rotatable knob 1410 until release occurs. Distal end 1402 is configured to releasably connect to the back/proximal end of the implant 1480 and, preferably, also release from the further rotation of knob 1410.

Another embodiment of the invention relates to an insert tool comprising a rotatable knob connected to a shaft comprising a first shaft and second shaft, wherein the rotatable knob is configured to translate the first shaft relative to the second shaft to allow for pivoting of an implant connected to the distal end of the tool. Preferably, the shaft comprises a channel opening configured for insertion of a driver tool.

Another embodiment of the invention relates to an insert tool comprising a rotatable knob connected to a shaft having a distal end configured to reversibly connect to an implant, wherein the rotation of the knob is configured to allow the shaft to pivot the implant.

According to preferred embodiments, the shaft comprises a hollow or open channel to allow for insertion of a driver tool configured to rotate the center rod of the implant.

The scope of the present devices, systems and methods, etc., includes both means plus function and step plus function concepts. However, the claims are not to be interpreted as indicating a "means plus function" relationship unless the word "means" is specifically recited in a claim, and are to be interpreted as indicating a "means plus function" relationship where the word "means" is specifically recited in a claim. Similarly, the claims are not to be interpreted as indicating a "step plus function" relationship unless the word "step" is specifically recited in a claim, and are to be interpreted as indicating a "step plus function" relationship where the word "step" is specifically recited in a claim.

Moreover, the various features of the representative examples and the dependent claims may be combined in ways that are not specifically and explicitly enumerated in order to provide additional useful embodiments of the present teachings. It is also expressly noted that all value ranges or indications of groups of entities disclose every possible intermediate value or intermediate entity for the purpose of original disclosure, as well as for the purpose of restricting the claimed subject matter. It is also expressly noted that the dimensions and the shapes of the components shown in the figures are designed to help to understand how the present teachings are practiced, but not intended to limit the dimensions and the shapes shown in the examples. It is understood that the embodiments described herein are for the purpose of elucidation and should not be considered limiting the subject matter of the disclosure. Various modifications, uses, substitutions, combinations, improvements, methods of productions without departing from the scope or spirit of the present invention would be evident to a person skilled in the art.

The invention claimed is:

1. An expandable intervertebral spine implant having an anterior side, a posterior side, a distal end and a proximal end, the implant comprising:

(a) a center rod having a center rod length comprising a proximal threaded portion having a proximal threading direction and a distal threaded portion having a distal threading direction opposite the proximal threading direction;

(b) a proximal sled coupled to the proximal threaded portion and a distal sled coupled to the distal threaded portion;

(c) at least one pair of anterior side plates comprising an anterior side top plate and an anterior side bottom plate, wherein said anterior side top plate is reversibly connected to said anterior side bottom plate and wherein each anterior side plate is discrete from, and oppose, each other; and (d) at least one pair of posterior side plates comprising a posterior side top plate and a posterior side bottom plate, wherein said posterior side top plate is reversibly connected to said posterior side bottom plate and wherein each posterior side plate is discrete from, and oppose, each other;

wherein when the center rod is rotated in a first rotation direction, the distal sled and the proximal sled move further apart relative to one another along the length of the center rod and wherein when the center rod is rotated in a second rotation direction opposite the first rotation direction the distal sled and the proximal sled move closer along the length of center rod; and wherein the expandable intervertebral spine implant is configured so that:

(i) when the distal sled and the proximal sled are positioned closest to each other within a central portion of the center rod, the implant is in a compact position;

(ii) when the distal sled and the proximal sled move farther apart along a first length in each direction from the center portion of the center rod, the anterior side plates and the posterior side plates move farther apart from one another and from the center rod thereby expanding the implant in a first expansion direction; and (iii) when the distal sled and the proximal sled move farther apart from the center portion along a second length of the center rod, the anterior side top plate and the anterior side bottom plate move apart from one another thereby expanding the implant on the anterior side in a second expansion direction; and wherein:

(I) the anterior side top plate is configured to reversibly slide into or onto the anterior side bottom plate;

(II) wherein the anterior side top plate and the anterior side bottom plate each comprise a side comprising a flat horizontal central portion, a stepped-up portion on each side of the flat horizontal central portion and a ramping portion on each end of the stepped-up portion opposite the flat horizontal central portion.

2. The implant of claim 1, wherein the second expansion direction results in an expansion in width and angulation to restore lordosis.

3. The implant of claim 1, wherein the distal sled is connected to an anterior side distal articulating arm and a posterior side distal articulating arm and wherein the anterior side distal articulating arm and the posterior side distal articulating arm are configured to articulate relative to the distal sled.

4. The implant of claim 1, wherein the proximal sled is connected to an anterior side proximal articulating arm and a posterior side proximal articulating arm and wherein the anterior side proximal articulating arm and the posterior side proximal articulating arm are configured to articulate relative to the proximal sled.

5. The implant of claim 4, wherein the anterior side distal articulating arm and the anterior side proximal articulating arm are configured to move the anterior side plates.

6. The implant of claim 4, wherein the posterior side distal articulating arm and the posterior side proximal articulating arm are configured to move the posterior side plates.

7. The implant of claim 1, wherein the anterior side top plate has an anterior side top plate length in a direction from the distal end to the proximal end and the anterior side bottom plate has an anterior side bottom plate length in the direction from the distal end to the proximal end and wherein the anterior side top plate length is different than the anterior side bottom plate length.

8. The implant of claim 1, wherein the anterior side top plate is configured to reversibly slide into or over the anterior side bottom plate.

9. The implant of claim 1, wherein the anterior side top plate and the anterior side bottom plate each have a U-shaped side profile and the U-shape of the anterior side top plate is configured to reversibly slide into or over the U-shape of the anterior side bottom plate.

10. The implant of claim 9, wherein the U-shape of the anterior side top plate and the U-shape of the anterior side bottom plate are configured so that (a) when the pairs of opposing articulating arms are positioned within the flat horizontal bottom of each anterior side plate and the anterior side plates and posterior side plates are positioned closest to one another resulting in a compact implant for insertion; (b) when the pair of opposing articulating arms are positioned within the step-up portion the anterior side plates and the anterior side plates and the posterior side plates are positioned further apart from one another thus expanding the implant in a first direction; and (c) when the pair of opposing articulating arms are positioned within the angled ramping portion of each anterior side plate, the anterior side top plate and the anterior side bottom plate are positioned still further apart from one another and thus expanding the implant in a second direction.

11. The implant of claim 10, wherein the U-shape of the anterior side top plate and the U-shape of the anterior side bottom plate are configured so that when the pair of opposing articulating arms are positioned within the angled ramping portion of each anterior side plate, the posterior side plates are positioned closer to the center rod.

12. The implant of claim 10, wherein the U-shape of the anterior side top plate and the U-shape of the anterior side bottom plate are configured so that when the pair of opposing articulating arms are positioned within the angled ramping portion of each anterior side plate, posterior side plate and posterior side plate are rotated relative to each other.

13. The implant of claim 1, wherein said implant has dimensions and configuration adapted to allow the implant to be inserted into an intervertebral disc space via Kambin's Triangle via an oblique lateral approach approximately 45 degrees off midline.

14. The implant of claim 1, further comprising a frame that is configured to couple to the center rod, the distal sled and the proximal sled.

15. The implant of claim 14, wherein the frame comprises a frame distal end having an insertion component configured to facilitate insertion of the implant into an intervertebral disc space and a frame proximal end including a socket or opening configured for receipt of an insert tool to rotate the center rod.

16. The implant of claim 15, wherein the frame proximal end comprises an opening configured to (a) allow an insert tool to secure and pivot the implant within the intervertebral disc space and (b) to contact and rotate the proximal end of the center rod.

17. The implant of claim 1, wherein the proximal threaded portion of center rod comprises a proximal end and a distal end, wherein the proximal end comprises a recess configured for receipt of an insert tool to rotate the center rod and the distal end comprises a prong configuration to connect to the distal threaded portion.

18. A method for stabilizing a spinal unit of a spinal column of a subject, the spinal unit comprising a superior vertebral bone, an inferior vertebral bone, an intervertebral disc space disposed there between, the method comprising:

(a) forming a skin incision in the subject;

(b) extending a tissue corridor from the skin incision to the intervertebral disc space through a Kambin's triangle opening formed by a superior endplate of an inferior vertebral bone, superior articular process of an inferior vertebral bone and a path of a spinal nerve and a first vertical axis that extends, in a cephalad to caudad direction, along a vertical plane of a spinal column;

(c) approaching the intervertebral disc space with the implant of claim 1 using an insert tool, wherein the central rod is rotated and positioned so that the distal sled and the proximal sled are close to the central portion of the center rod thus reducing the dimensions of the implant for insertion;

(d) seating the implant within the intervertebral disc space using the insert tool;

(e) rotating the center rod using the insert tool to move the distal sled and the proximal sled farther apart along a first length from a center portion of the center rod and thus moving the anterior side plates and the posterior side plates farther apart from one another and from the center rod thereby expanding the implant in a first expansion direction;

(f) further rotating the center rod using the insert tool to move the distal sled and the proximal sled farther apart from a center portion along a second length of the center rod and thus move the anterior side top plate and the anterior side bottom plate apart from one another thereby expanding the implant on the anterior side in a second expansion direction; and (g) removing the insert tool.

19. The method of claim 18, further comprising, after the step of seating the implant in the intervertebral disc space, pivoting the implant within the intervertebral disc space.

20. An expandable intervertebral spine implant having an anterior side, a posterior side, a distal end and a proximal end, the implant comprising:

(a) a center rod having a center rod length comprising a proximal threaded portion having a proximal threading direction and a distal threaded portion having a distal threading direction opposite the proximal threading direction;

(b) a proximal sled coupled to the proximal threaded portion and a distal sled coupled to the distal threaded portion;

(c) at least one pair of anterior side plates comprising an anterior side top plate and an anterior side bottom plate, wherein said anterior side top plate is reversibly connected to said anterior side bottom plate and wherein each anterior side plate is discrete from, and oppose, each other; and (d) at least one pair of posterior side plates comprising a posterior side top plate and a posterior side bottom plate, wherein said posterior side top plate is reversibly connected to said posterior side bottom plate and wherein each posterior side plate is discrete from, and oppose, each other;

wherein when the center rod is rotated in a first rotation direction, the distal sled and the proximal sled move further apart relative to one another along the length of the center rod and wherein when the center rod is rotated in a second rotation direction opposite the first rotation direction the distal sled and the proximal sled move closer along the length of center rod; and wherein the expandable intervertebral spine implant is configured so that:

(i) when the distal sled and the proximal sled are positioned closest to each other within a central portion of the center rod, the implant is in a compact position;

(ii) when the distal sled and the proximal sled move farther apart along a first length in each direction from the center portion of the center rod, the anterior side plates and the posterior side plates move farther apart from one another and from the center rod thereby expanding the implant in a first expansion direction; and (iii) when the distal sled and the proximal sled move farther apart from the center portion along a second length of the center rod, the anterior side top plate and the anterior side bottom plate move apart from one another thereby expanding the implant on the anterior side in a second expansion direction and the posterior side top plate angulates relative to the posterior side bottom plate; and wherein (I) the distal sled is connected to an anterior side distal articulating arm and a posterior side distal articulating arm and wherein the anterior side distal articulating arm and the posterior side distal articulating arm are configured to articulate relative to the distal sled; and (II) the proximal sled is connected to an anterior side proximal articulating arm and a posterior side proximal articulating arm and wherein the anterior side proximal articulating arm and the posterior side proximal articulating arm are configured to articulate relative to the proximal sled.

21. An expandable intervertebral spine implant having an anterior side, a posterior side, a distal end and a proximal end, the implant comprising:

(a) a center rod having a center rod length comprising a proximal threaded portion having a proximal threading direction and a distal threaded portion having a distal threading direction opposite the proximal threading direction;

(b) a proximal sled coupled to the proximal threaded portion and a distal sled coupled to the distal threaded portion;

(c) at least one pair of anterior side plates comprising an anterior side top plate and an anterior side bottom plate, wherein said anterior side top plate is reversibly connected to said anterior side bottom plate and wherein each anterior side plate is discrete from, and oppose, each other; and (d) at least one pair of posterior side plates comprising a posterior side top plate and a posterior side bottom plate, wherein said posterior side top plate is reversibly connected to said posterior side bottom plate and wherein each posterior side plate is discrete from, and oppose, each other;

wherein when the center rod is rotated in a first rotation direction, the distal sled and the proximal sled move further apart relative to one another along the length of the center rod and wherein when the center rod is rotated in a second rotation direction opposite the first rotation direction the distal sled and the proximal sled move closer along the length of center rod; and wherein the expandable intervertebral spine implant is configured so that:

(i) when the distal sled and the proximal sled are positioned closest to each other within a central portion of the center rod, the implant is in a compact position;

(ii) when the distal sled and the proximal sled move farther apart along a first length in each direction from the center portion of the center rod, the anterior side plates and the posterior side plates move farther apart from one another and from the center rod thereby expanding the implant in a first expansion direction; and (iii) when the distal sled and the proximal sled move farther apart from the center portion along a second length of the center rod, the anterior side top plate and the anterior side bottom plate move apart from one another thereby expanding the implant on the anterior side in a second expansion direction; and wherein the anterior side top plate has an anterior side top plate length in a direction from the distal end to the proximal end and the anterior side bottom plate has an anterior side bottom plate length in the direction from the distal end to the proximal end and wherein the anterior side top plate length is different than the anterior side bottom plate length and wherein the anterior side bottom plate is configured to reversibly slidably fit within the anterior side top plate or the anterior side top plate is configured to reversibly slidably fit within the anterior side bottom plate.

* * * * *